(12) United States Patent
Edwards et al.

(10) Patent No.: US 6,790,607 B1
(45) Date of Patent: Sep. 14, 2004

(54) ADJUSTABLE SENSITIVITY, GENETIC MOLECULAR INTERACTION SYSTEMS, INCLUDING PROTEIN-PROTEIN INTERACTION SYSTEMS FOR DETECTION AND ANALYSIS

(75) Inventors: David N. Edwards, Addison, TX (US); Arlene Leon, Garland, TX (US); David F. Ranney, Dallas, TX (US)

(73) Assignee: Hybrigen, Inc., Dallas, TX (US)

( * ) Notice: Subject to any disclaimer, the term of this patent is extended or adjusted under 35 U.S.C. 154(b) by 0 days.

(21) Appl. No.: 09/680,738

(22) Filed: Oct. 6, 2000

Related U.S. Application Data
(60) Provisional application No. 60/158,079, filed on Oct. 7, 1999.

(51) Int. Cl.[7] .................................................. C12Q 1/00

(52) U.S. Cl. ..................... 435/4; 435/69.1; 435/69.7; 435/71.1; 435/6

(58) Field of Search .............................. 435/4, 6, 69.1, 435/69.7, 71.1

(56) References Cited

U.S. PATENT DOCUMENTS

| 5,925,523 A | * | 7/1999 | Dove et al. |
| 5,965,368 A | | 10/1999 | Vidal et al. |

FOREIGN PATENT DOCUMENTS

| WO | 97/31113 | 8/1997 | ........... C12N/15/12 |

OTHER PUBLICATIONS

International Search Report PCT/US 00/27677, Feb. 15, 2002.
Ammerer, G.; 1983. Expression of genes in yeast using the ACDI promoter. Methods in Enzymol. 101, 192–201.
Aronheim, A.; Zandi, E.; Hennemann, H.; Elledge, S. J.; and Karin, M.; 1997. Isolation of an AP–1 Repressor by a Novel Method for Detecting Protein–Protein Interactions. Mol. Cell. Biol. 17, 3094–3102.
Bai, C.; and Elledge, S. J.; 1997. Gene Identification Using the Yeast Two–Hybrid System. Methods Enzymol. 283, 141–156.
Baldwin, A. S.; 1996. The NF–κB and IκB Proteins: New Discoveries and Insights. Annu. Rev. Immunol. 14, 649–681.
Bartel, P.; Chien, C.; Sternglanz, R.; and Fields, S.; 1993. Elimination of False Positives That Arise in Using the Two–Hybrid System. Biotechniques 14, 920–924.
Berridge, P.; Lipp, P.; and Bootman, M.; 1999. Calcium signalling. Curr. Biology 9, R157–R159.
Brachmann, R. K.; and Boeke, J. D.; 1997. Tag games in yeast: the two–hybrid system and beyond. Curr. Opin. Biotechnol. 8, 561–568.
Bunker, C. A.; and Kingston, R. E.; 1995. Identification of a cDNA for SSRP1, an HMG–box protein, by interaction with the c–Myc oncoprotein in a novel bacterial expression screen. Nucleic Acid Res. 23, 269–276.
Bustos, S. A.; and Schleif. R. F.; 1993. Functional domain of the AraC protein. Proc. Natl. Acad. Sci. 90, 5368–5642.
Cantwell, B. A.; Brazil, G.; Murphy, N.; and McConnell, D. J.; 1986. Comparison of expression of the endo–β–1,3–1, 4–glucanase gene from *Bacillus subtilis* in *Saccharomyces cerevisiae* from the CYC1 and ADH1 promoters. Curr. Genetics 11, 65–70.
Edwards, D. N.; Towb, P.; and Wasserman, S. A.; 1997. An activity–dependent network of interactions links Rel protein Dorsal with its cytoplasmic regulators. Development 124, 3855–3864.
Estojak, J.; Brent, R.; and Golemis, E. A.; 1995. Correlation of Two–Hybrid Affinity Data with In Vitro Measurements. Mol. Cell. Biol. 15, 5820–5829.
Fearon, E. R.; Finkel, T.; Gillison, M. L.; Kennedy, S. P.; Casella, J. F.; Tomaselli, G. F.; Morrow, J. S.; and Van Dang, C.; 1992. Karyoplasmic interaction selection strategy: A general strategy to detect protein–protein interactions in mammalian cells. Proc. Natl. Acad. Sci. 89, 7958–7962.
Fields, S.; and Song, O.; 1989. A novel genetic system to detect protein–protein interactions. Nature 340, 245–246.
Finley, R. L.; and Brent, R.; 1997. Two–hybrid analysis of genetic regulatory networks. In: The Yeast Two–Hybrid System. Ed. Bartel, P. L.; Fields, S.; pp. 197–214, Oxford Univ. Press.
Gaido, K. W.; Leonard, L. S.; Lovell, S.; Gould, J. C. babai, D.; Portier, C. J.; and McDonell, D. P.; 1997. Evaluation of chemicals with endocrine modulating activity in a yeast based steroid hormone receptor gene transcription assay. Toxic. and App. Pharm. 143, 205–212.
Guarente, L.; 1983. Yeast Promoters and lacZ Fusions Designed to Study Expression of Cloned Genes in Yeast. Methods in Enzymol. 101, 181–191.
Guarente, L.; and Ptashne, M.; 1981. Fusion of *Escherichia coli* lacZ to the cytochrome c gene of *Saccharomyces cerevisiae*. Proc. Natl. Acad. Sci. 78, 2199–2203.
Guarente, L.; Yocum, R. R.; and Gifford, P.; 1982. A GAL10 hybrid yeast promoter identifies the GAL4 regulatory region as an upstream site. Proc. Natl. Acad. Sci. 79, 7410–7414.
Gyuris, J.; Golemis, E.; Chertkov, H; and Brent, R.; 1993. Cdi1, a Human G1 and S Phase Protein Phosphatase That Associates with Cdk2. Cell 75, 791–803.

(List continued on next page.)

Primary Examiner—James Ketter
Assistant Examiner—David Lambertson
(74) Attorney, Agent, or Firm—Baker Botts L.L.P.

(57) ABSTRACT

A method for detecting interactions between first and second interacting molecules at variable sensitivity. This variable sensitivity may be obtained by providing for the overexpression of either a bait hybrid protein containing a DNA binding domain (desensitization) or a prey hybrid protein containing the DNA activation domain for a reporter gene (enhanced sensitivity). The use of exogenous activators of one or the other according to the needs of a particular system is readily accomplished.

4 Claims, 2 Drawing Sheets

OTHER PUBLICATIONS

Hays, L. B.; Chen, Y–S. A.; and Hu, J. C.; 2000. Two–hybrid screen for characterization of protein–protein interactions in *E. coli*. Biotechniques, 29, 288–294.

James, P.; Halladay, J.; and Craig, E. A.; 1996. Genomic Libraries and a Host Strain Designed for Highly Efficient Two–Hybrid Selection in Yeast. Genetics 144, 1425–1436.

Kliewer, S. A.; Lehmann, J. M.; and Willson, T. M.; 1999. Orphan Nuclear Receptors: Shifting Endocrinology into Reverse. Science 284, 757–760.

Kralli, A.; Bohen, S. P.; and Yamamoto, K. R.; 1995. LEM1, an ATP–binding–cassette transporter, selectively modulates the biological potency of steroid hormones. Proc. Natl. Acad. Sci. 92, 4701–4705.

Li, J. J.; and Herskowitz, I.; 1993. Isolation of ORC6, a Component of the Yeast Origin Recognition Complex by a One–Hybrid System. Science 262. 1870–1874.

Mangelsdorf, D. J.; and Evans, R. M.; 1995. The RXR Heterodimers and Orphan Receptors. Cell 83, 841–850.

Mangus, D. A.; Amrani, N.; and Jacobson, A.; 1998. Pbp1p, a Factor Interacting with *Saccharomyces cerevisiae* Poly-(A)–Binding Protein, Regulates Polyadenylation. Mol. Cell. Biol. 18, 7383–7396.

Martinez, A.; Sparks, C.; Drayton, P.; Thompson, J.; Greenland, A.; and Jepson, I.; 1999. Creation of ecdysone receptor chimeras in plants for controlled regulation of gene expression. Mol. Gen. Genet. 261, 546–552.

Mendelsohn, A. R.; and Brent, R.; 1994. Applications of interaction traps/two–hybrid systems to biotechnology research. Curr. Opin. Biotechnol. 5, 482–486.

Mercurio, F.; and Manning, A. M.; 1999. Multiple signals converging on NF–κB. Curr. Opin. Cell. Biol. 11, 226–232.

Moghal, N.; and Sternberg, P. W.; 1999. Multiple positive and negative regulators of signaling by the EGF–receptor. Curr. Opin. Cell. Biol. 11, 190–196.

Phizicky, E. M.; and Fields, S.; 1995. Protein–Protein Interactions: Methods for Detection and Analysis. Microbiological Reviews, vol. 59k, No. 1, pp. 94–123.

Picard, D.; Khursheed, B.; Garabedian, M. J.; Fortin, M. G.; Lindquist, S.; and Yamamoto, K. R.; 1990. Reduced levels of hsp90 compromise steroid receptor action in vivo. Nature 348, 166–168.

Rossi, F. M.V.; and Blau, H. M.; 1998. Recent advances in inducible gene expression systems. Curr. Opin. Biotechnol. 9, 451–456.

Schena, M.; Picard, D.; and Yamamoto, K. R.; 1991. Vectors for Constitutive and Inducible Gene Expression in Yeast. Methods in Enzymol. 194, 389–398.

Schena, M.; and Yamamoto, K. R.; 1988. Mammalian Glucocorticoid Receptor Derivatives Enhance Transcription in Yeast. Science 241, 965–967.

SenGupta, D. J.; Zhang, B.; Kraemer, B.; Pochart, P.; Fields, S.; and Wickens, M.; 1996. A three–hybrid system to detect RNA–protein interactions in vivo. Proc. Natl. Acad. Sci. 93, 8496–8501.

Serebriiskii, I.; Khazak, V.; and Golemis E. A.; 1999. A two–hybrid dual system to discriminate specificity of protein interactions. J. Biol. Chem. 274(24), 17080–17087.

Shioda, T.; Andriole, S; Yahata, T.; and Isselbacher, K. J.; 2000. A green fluorescent protein–reporter mammalian two–hybrid system with extrachromosomal maintenance of a prey plasmid: Application to interaction screening. Proc. Natl. Acad. Sci. 97, 5220–5224.

Vasavada, H. A.; Ganguly, S.; Germino, F. J.; Wang, Z. X.; and Weissman, S. M.; 1991. A contingent replication assay for the detection of protein–protein interactions in animal cells. Proc. Natl. Acad. Sci. 88, 10686–10690.

West, R. W., Jr.; Yocum, R. R.; and Ptashne, M.; 1984. *Saccharomyces cerevisiae* GAL1–GAL10 Divergent Promoter Region: Location and Function of the Upstream Activating Sequence $UAS_G$. Mol. Cell. Biol. 4, 2467–2478.

Yang, M; Wu, Z.; and Fields, S.; 1995. Protein–peptide interactions analyzed with the yeast two–hybrid system. Nucleic Acid Res. 23, 1152–1156.

Young, K. H.; 1998. Yeast Two–Hybrid: So Many Interactions, (in) So Little Time . . . Biology of Reproduction 58, 302–311.

\* cited by examiner

ADJUSTABLE SENSITIVITY, GENETIC MOLECULAR INTERACTION SYSTEMS, INCLUDING PROTEIN-PROTEIN INTERACTION SYSTEMS FOR DETECTION AND ANALYSIS

CROSS-REFERENCE TO RELATED REFERENCES

Priority is claimed from provisional application U.S. Serial No. 60/158,079 filed on Oct. 7, 1999 and incorporated by reference herein.

BACKGROUND OF THE PRESENT INVENTION

Genetically-based interaction systems are commonly used in scientific research and in commercial and therapeutic applications derived from that research. Current genetically-based interaction systems are severely limited by a fixed level of interaction sensitivity which is either completely "on" or completely "off" (Fields and Song, 1989; Bartel et al., 1993; Gyuris et al., 1993; Mendelsohn and Brent, 1994; Phizicky and Fields, 1995; Bai and Elledge, 1997; Brachmann and Boeke, 1997; Finley and Brent, 1997; Young, 1998). This creates problems related to both the detection of numerous biologically irrelevant interactions, as well as a failure to detect relevant biological interactions. The consequences of this problem may be either a complete inability or prolonged time required to elucidate important biologically relevant interactions, cellular pathways, and potentially related modulatory agents and drugs.

Historically, the first description of a genetic system to detect molecular interactions is the two-hybrid system (Fields and Song, 1989; FIG. 1). This set forth the original concept and practice of detecting protein-protein interactions in *Saccharomyces cerevisiae*. This original system features detection of an in vivo protein-protein interaction within the nucleus of the yeast cells. These cells were engineered to express the visually detectable bacterial gene lacZ in the presence of an interaction. Basically, the host cells were transformed with an expressible gene coding for a first hybrid protein composed of a DNA binding domain and a first polypeptide. The host cells were additionally transformed with a second hybrid protein consisting of a transcriptional activation domain and a second polypeptide of stable interaction with the first protein fragment. Finally, the cells were also transformed with a lacZ reporter gene containing at least one DNA binding sequence for the DNA binding domain of the first hybrid protein and capable of being transcribed at increased and detectable levels when the transcriptional activation domain of the second hybrid protein was in close proximity. Field and Song demonstrated that when the two hybrid proteins were expressed, levels of the LacZ reporter protein dramatically increased in the host cell. This indicated that the DNA binding domain in the first hybrid protein was binding to the DNA binding sequence of the reporter gene and that the first polypeptide of the first hybrid protein was interacting with the second polypeptide of the second hybrid protein in such a manner as to bring the transcriptional activation domain of the second hybrid protein into proximity of the lacZ gene and thus increase its transcription and subsequent expression.

This basic approach has been employed in all later two-hybrid and three-hybrid systems. Extensions of this work describe such detection capability in nuclear, cytoplasmic, or membrane locations of eukaryotes (Aronheim et al., 1997; Gyuris et al., 1997), as well as in prokaryotes (Bustos and Schleif, 1993; Bunker and Kingston, 1995; Hays et al., 2000). The initial art has also been subsequently extended to include multiple prokaryotic (Bustos and Schleif, 1993; Bunker and Kingston, 1995; Hays et al., 2000) and eukaryotic organisms (other fungal strains, arthropod, plant, and mammalian cells) (e.g. Vasavada et al., 1991; Fearon et al., 1992; Luo et al., 1997; Shoda et al., 2000).

Parallel approaches to genetic molecular interaction detection have been described for detecting protein interactions with RNA and DNA, as well as with small ligands, including peptides and drugs (Li and Herskowitz, 1993; Yang et al., 1995; SenGupta et al., 1996; Brachmann and Boeke, 1997; Young, 1998). All of these systems work on the same basic concept of using the living cell as a means of detecting the interaction between two intracellular molecules.

Genetic molecular detection systems following the original Fields two-hybrid system also usually include the additional feature of genetic selection (Fields and Song, 1989). Selection allows the detection of an interaction by choosing the phenotype of survival; cells containing proteins that do not interact strongly enough or at all are unable to grow, and are no longer considered. The current methods of selection are limited to an "all or nothing" auxotrophic nutrient, antibiotic selection or other means of affecting survival (Fields and Song, 1989; Gyuris et al., 1993; Bai and Elledge, 1997). Selection yields a great advantage for the various detection systems, since cells containing potentially irrelevant pairs of candidate interacting molecules are eliminated without intervention from the scientist or other automated analysis.

However, the introduction of genetic selection introduced a new and severely limiting aspect to the in vivo genetic molecular detection systems. All current methods of selecting for molecular interactions in vivo must make a priori assumptions about the strength of the interactions that they detect. The system must be constructed such that there is a threshold above which an interaction will be detected, and below which it will not. That is, there is an implicit assumption that very weak or transient interactions are probably less likely to be real or important. Systems are designed to exclude these interactions because, if systems are too sensitive, they will detect too much background. However, if the system is not sensitive at all, important interactions will be missed. Those constructing these systems built them and tested them, and then used the systems with the most reasonable compromise of detection sensitivity. In short, they chose the compositions that yielded, on average, a tolerable background while missing a tolerable number of biologically relevant interactions.

Early crude attempts to overcome this "all or nothing" threshold of reporting output have included: (a) exposure of yeast to toxic nutrient analogues at sub-lethal concentrations, for example. 3-AT as a histidine synthesis inhibitor (Mangus et al., 1998); and (b) the creation of complicated genetic modifications of the reporter, which gives several different fixed (nonadjustable) levels of detection (James et al., 1996; Finley and Brent, 1997; Serebriiskii et al., 1999). Such complicated modifications include the use of (b.1.) variable numbers of reporter binding sites, (exemplified by the use of multiple LexA binding sites (by, e.g. multiple LexA binding sites for a Leucine reporter as described in Finley and Brent, 1997), for a Leucine reporter as described in Finely and Brent, 1997), and (b.2) variable distance between reporter building site and the transcriptional start site (West et al., 1984).

A feature of current detection systems is the capacity to turn the detection of protein interactions on or off completely by providing for the expression or lack of expression of the two-hybrid library fusion under standard nutrient conditions. Gyuris et al. (1993) found that by being able to express one of the two hybrid proteins at high levels or by being able to limit expression of one such protein completely, it was possible to show in vivo that the presence of both of the hybrid proteins were necessary for activation of the reporter gene; in other words, they added a switch enabling on or off control of one of the interacting components. This control is useful and exerts its effects by modulating reporter activity, but it does not provide for the continuous adjustability of the sensitivity of a two-hybrid protein interaction system. Thus, the Gyuris system further demonstrates the limitation of the prior art; it is either on or off, above or below the same detection threshold set by the reporters chosen when the system was constructed.

The level of reporter gene expression that will result from any given molecule-molecule interaction in a two-hybrid system is uniform for those molecules used in combination with that reporter. The Brent lab first demonstrated this in experiments using a traditional two-hybrid protein-protein interaction system. The experiments showed that output of the quantitative lacZ reporter was directly proportional to the independently determined strength (or Kd) of the protein-protein interaction for the protein fragments used in the hybrid proteins. If the two proteins interacted strongly in vitro, they gave robust expression from the two-hybrid reporters and vice versa. Therefore, they also demonstrated that the output of a given reporter is constant for a given part of interacting proteins. This is now generally accepted, since many publications of genetic molecular interactions include the quantitative reporter output from the interaction system as a relative indication of the strength of the interaction itself (Edwards et al. 1997).

The present invention yields surprising and unexpected advantages relative to earlier systems in providing for adjustability of the sensitivity of such detection systems.

SUMMARY OF THE INVENTION

The present invention comprises an improved two-hybrid or three-hybrid detection method and a kit utilizing this method. The method of the current invention may be used with any conventional two-hybrid or three-hybrid methods, including inhibition or competition two-hybrid methods, as well as any future variations of those methods. In all embodiments of the present invention, the sensitivity of a detectable reporter gene in a host cell is continuously adjustable by altering the relative or absolute amounts of interacting molecules provided to the host cell. The method may be used to detect interactions between any types of molecules including, but not limited to, proteins, polypeptides, DNA molecules, RNA molecules, pharmaceutical agents, other biological or chemical agents, and other small molecules or macromolecules. The method may be used to detect interactions in both prokaryotic and eukaryotic organisms or cells. The molecular interactions may occur at various locations, including, but not limited to, extracellular regions, the cell membrane, the cytoplasm, the nuclear membrane, the nucleus, and other intracellular regions.

In a preferred embodiment, the first chimeric gene and the second chimeric gene are introduced into the host cell. The host cell is then subjected to conditions under which a first hybrid protein and a second hybrid protein are expressed in at least sufficient quantities for the detectable reporter gene within the host cell to be activated. The first chimeric gene contains a first exogenously activatable promoter and a sequence encoding the first hybrid protein. The first hybrid protein contains a DNA binding domain capable of binding near the reporter gene and a first interacting polypeptide (bait). The second chimeric gene contains a second exogenously activatable promoter and a sequence encoding a second hybrid protein. The second hybrid protein contains a transcriptional activation domain capable of inducing or increasing transcription of the reporter gene and a second interacting polypeptide(prey). This second polypeptide may be derived from a library.

The sensitivity of the reporter gene may be altered by adding a first and/or second exogenous activator and thus, altering the relative or absolute amounts of the first and/or second hybrid proteins. These alterations affect the activity and thus sensitivity of the report gene. The sensitivity of this activation may be decreased by adding a first exogenous activator capable of activating the first exogenous promoter. This results in increased production of the first hybrid protein and raises its level in the host cell relative to the level of the second hybrid protein. Thus, after this increase, more DNA binding sites of the reporter gene are occupied by the first hybrid proteins for which there is not second hybrid protein available for interaction. Therefore, less of the reporter genes are activated or activation is weaker.

The sensitivity of the reporter activation may be increased by adding a second exogenous activator capable of activating the second exogenous promoter. This results in increased production of the second hybrid protein and raises its level in the host cell relative to the level of the first hybrid protein. Thus, after this increase, more of the DNA binding sites of the reporter gene are occupied by a first hybrid protein that is additionally interacting with a second hybrid protein. Therefore, more of the reporter genes are activated or activation is stronger. Subsequent to the hybrid protein expressions, detectable reporter gene expression is measured and compared to the amount of expression in the absence of any interaction between the first test protein and the second test protein.

A kit utilizing the method of this invention may also be prepared. The kit may comprise any host cell described above, any first or second chimeric genes described above, or any combination thereof. The kit may also contain the first and second exogenous activators and also chemicals or assays for detecting the detectable reporter gene product.

CYC1p=CYC1 promoter from yeast; Gal4AD=Gal4 activation domain; AdhT=Alcohol dehydrogenase terminator.

Figure 3:
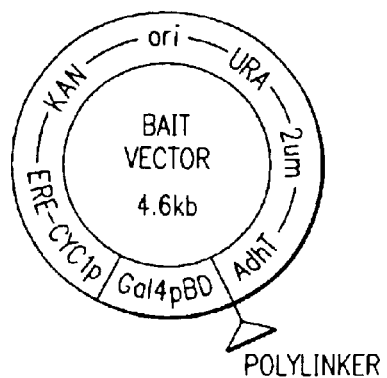

FIG. 3 shows the novel Bait vector in a shuttle vector containing kanamycin and the colE1 origin of replication for selection in *E.coli* as well as URA3 and the 2 um origin of replication for selection in yeast. A known cDNA is fused to the Gal4p DNA binding domain, and continuously variable expression is obtained by the induction of ERE element(s) attached to CYC1 promoter. KAN=Kanamycin. *E.coli* selectable marker; ori=colE1 bacterial origin of replication; URA=URA3 gene, yeast selectable marker, 2 um=origin of replication for yeast; ERE=Estrogen Response Element; CYC1p=CYC1 promoter from yeast; Gal4pBD=Gal4p DNA binding domain; AdhT=Alcohol dehydrogenase terminator.

Figure 4:
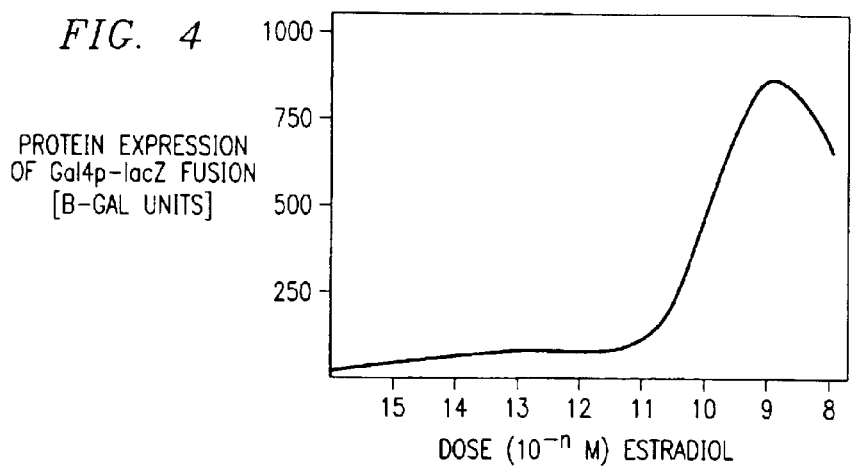

FIG. 4 shows a Continuously Dose Responsive Expression of proteins fused to Gal4pBD in the "Bait Vector" in yHYB001 strain. Strain yHYB001 with the bait vector is grown in selective minimal media with varying concentrations of estradiol. The bait vector contains the Gal4pBD fused to the marker lacZ. β-gal expression assays are performed three times per estradiol concentration; the data represents an averaging of three assays per sample. Growth was overnight and strains were at $OD_{600}$ ca. 0.8 when assayed. Strain yHYB001 is described in the text. β-gal expression assays are described in Guarente (1983). The variable "n" in the x-axis label "Dose ($10^{-n}$) dexamethasone" represents any given number on the x-axis.

Figure 5:
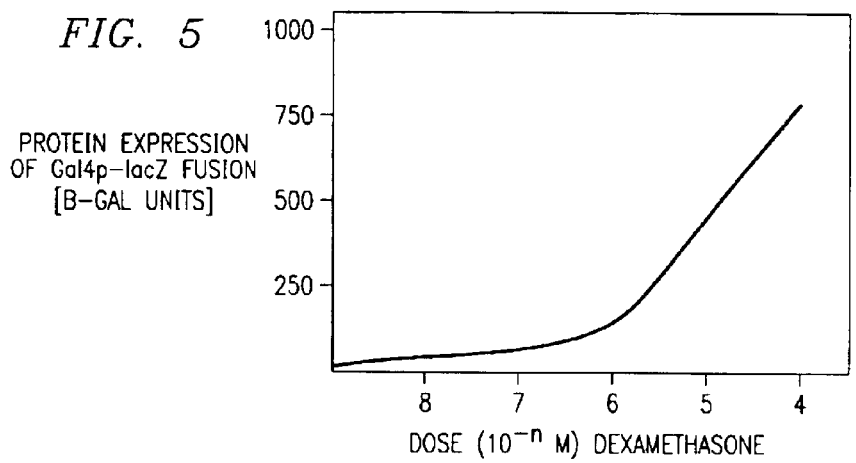

FIG. 5 shows Continuously Dose Responsive Expression of proteins fused to Gal4pAD in the "Library Vector" in yHYB001 strain. Strain yHYB001 with the library vector is grown in selective minimal media with varying concentrations of dexamethasone. The library vector contains the Gal4pAD fused to the marker lacZ. β-gal expression assays are performed three times per dexamethasone concentration; the data represents an averaging of three assays per sample. Growth was overnight and strains were at $OD_{600}$, ca. 0.8 when assayed. Strain yHYB001 is described in the text, β-gal expression assays are described in Guarente (1983). The variable "n" in the x-axis labeled "Dose ($10^{-n}$) dexamethasone" represents any given number on the x-axis.

Figure 6:
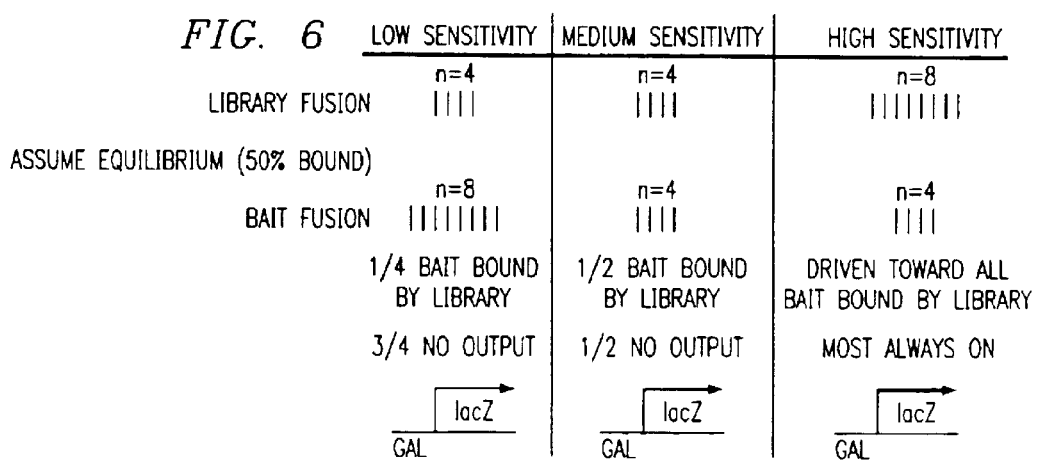

FIG. 6 shows the Principle of Variable Reporter Output with changes in relative concentration of interactors in a novel molecular genetic interaction detection system. The number of bars represent relative levels of library fusion protein and bait fusion protein present in the cell. At equilibrium, only a fraction of the fusion proteins will be physically paired at any given time, representing the Kd of the interaction (in this example, we assume 50% are bound at a given time.) A medium sensitivity assay results when both fusion proteins are present in roughly equal amounts. At equilibrium, half of them are interacting, resulting in an output that is ½ of the theoretical maximum from the reporter. This is true since half of the DNA-binding domain fusions at the reporter will not be paired to an activating library fusion. Lower sensitivity can be achieved by reducing the amount of library fusion and or increasing the amount of bait fusion. A two-fold difference in levels yields, at equilibrium, ¼ of he theoretical maximum from the reporter. High sensitivity results from an overabundance of library fusion; a two-fold excess at equilibrium will yield an output close to the theoretical maximum for the reporter.

DESCRIPTION OF THE PREFERRED EMBODIMENTS

Method to adjust the sensitivity of genetic macromolecular interaction systems.

This invention comprises novel compositions, methods and uses for continuously and or discontinuously adjusting the sensitivity of genetic detection systems to enable significantly improved detection and analysis of molecular interactions. The molecular interactions include those at extracellular, membrane and intracellular sites, and include but are not limited to protein-protein interactions, protein-DNA interactions, protein-RNA and protein-small molecule interactions in eukaryotic and prokaryotic organisms.

The method of the present invention involves changing the relative quantity of each macromolecular or small molecular component provided within the system, such that the absolute or relative amounts of actual interacting pairs changes within the system. By altering the relative amounts of interacting molecules (particularly the molecule bound to the detectable reporter gene), the output of the system via reporter gene expression is also altered.

In the method of the present invention, the host cell may be provided with a detectable reporter gene. This reporter gene may be provided before or after interacting molecules or other components are provided. However, the reporter gene is preferably provided first so that host cells that do not contain the reporter gene may be eliminated before interacting molecules or other components are introduced. The reporter gene may be provided through any method of gene transfer currently known or later developed. In a preferred embodiment, the reporter gene is provided through electroporation of the host cell. The reporter gene may also be provided in any form capable of transfer to the host cell using the selected transfer method. For instance, it may be provided as a portion of a plasmid.

Any detectable reporter gene that may be activated by an interaction of the interacting molecules is appropriate for this method. For instance, the reporter gene may produce a detectable reporter protein or other detectable gene product. The method of this invention can function with any detectable reporter gene because the method involves changing the amounts of the interacting macromolecules themselves. If there are more interaction to report, any reporter gene will report this as a relatively stronger activation of the reporter gene. If there are relatively fewer interactions to report, any reporter system will report this as a relatively weaker output.

In a preferred embodiment, the reporter gene comprises at least one DNA binding site capable of interaction with a polypeptide including a DNA binding domain or with another DNA binding molecule, such as a small molecule or pharmaceutical agent. This DNA binding site is located such that if a first interacting molecule binds to the site and additionally interacts with a second interacting molecule, the transcriptional activation domain of the second molecule will be able to activate transcription of the reporter gene.

A first interacting molecule which may be a macromolecule or small molecule into a host cell or its extracellular region. This molecule should contain a polypeptide containing a DNA binding domain or it should contain another molecular region capable of binding DNA. This first interacting molecule may be a protein, a DNA, a RNA, or a pharmaceutical agent or any other molecule that contains or may be bound to a molecule containing a DNA binding region or domain.

In a preferred embodiment, the molecule is a protein, a DNA, or a RNA. In such a preferred embodiment, the macromolecule is provided by introducing into the host cell a first chimeric gene capable of being transcribed in the host cell. This first chimeric gene may include a first exogenously activatable promoter, a sequence coding for a polypeptide, DNA, or RNA containing a DNA binding region, and a sequence coding for the first interacting macromolecule. In a more preferred embodiment, the first chimeric gene comprises a first exogenously activatable promoter and a first hybrid protein. This first hybrid protein comprises a DNA binding polypeptide and a first interacting polypeptide (bait) capable of interacting with at least one second interacting polypeptide (prey).

A second interacting macromolecule or small molecule is also introduced into the host cell or its extracellular region. This molecule should contain a transcriptional activation domain. This transcriptional activation domain may be a polypeptide or a region of another molecule capable of activating transcription such as a region of a pharmaceutical agent or a nucleic acid. In a preferred embodiment, this second molecule may be protein, a DNA, a RNA, a pharmaceutically agent, or any other molecule meeting the requirements stated above. In a more preferred embodiment it is a protein, a DNA, or a RNA. In such a preferred embodiment, the macromolecule may be produced in the host cell by introducing a second chimeric gene capable of being transcribed in the host cell. This second chimeric gene may include a second exogenously activatable promoter, a sequence coding for a transcriptional activation domain, and a sequence coding for the second macromolecule. In a more preferred embodiment, the chimeric gene may contain a second exogenously activatable promoter and a second hybrid protein. This second hybrid protein may contain a polypeptide containing a transcriptional activation domain and the second interacting polypeptide (prey).

In all embodiments of the present invention, the sensitivity of the detectable reporter gene in a host cell is continuously adjustable by altering the relative or absolute amounts of the first and/or second interacting molecules provided to the host cell. In a preferred embodiment, the host cell itself has the capacity to regulate the absolute of relative levels of the first or second molecules. As indicated in the preferred embodiments described above, this may be accomplished by introducing chimeric genes encoding the first and second macromolecules and containing first and second exogenously activatable promoters. These exogenously activatable promoters may be activated by exogenous activators.

While any promoters and activators may be used in the method of the present invention, in a more preferred embodiment, the activator is a natural or synthetic, metabolically active or inactive steroid, steroid analogue or minimic and the promoter induces transcription in response to the activator. The relative or absolute amount of at least one the hybrid proteins may then be controlled in a manner responsive to the dose of one or more of these activators, its analog, or its antagonist. Generally, if both chimeric genes are under the control of exogenously activatable promoters, the promoters will be different for each gene and will be activated by different molecules.

By regulating the relative levels of the first and second interacting molecules, it is possible to alter the sensitivity of the reporter. For instance, if the system is flooded with one component, usually the second molecule, it is possible to drive the system towards interaction of a first molecule bound to the reporter with a second molecule such that reporter activity is increased. At maximum sensitivity, every first molecule binding the reporter is involved in an interaction with a second molecule, and therefore the reporter is activated more often or more strongly.

It is also possible to dampen the output of the reporter by increasing the relative amount of one of the two interacting molecules, usually the first molecule. If this is done then most of the first molecules bound to the reporter are not additionally bound to a second molecule and thus the reporter activation is lowered.

Since the strength of a given interaction between any two molecules does not change, the capacity to regulate the relative to total amounts of either of the two interacting molecules results in a system that reports interaction at continuously adjustable levels of sensitivity. Thus, if an interaction is weak, sensitivity may be increased by increasing the relative number of interactions. Because there are more interactions, the reporter will report more strongly despite the weakness of the interactions. If an interaction is strong, sensitivity may be decreased by decreasing the relative number if interactions. Because there are fewer interactions, the reporter will report less strongly. Thus, interactions that might be deemed unimportant or undetectable using a conventional two-hybrid system may be detected with the present invention.

In another embodiment of the present invention, the cells may additionally be provided with other macromolecules or small molecules that mediate or interfere with the interactions between the first and second interacting molecules. For instance, in a three-hybrid system, a third macromolecule or small molecule may be provided that facilitates or is required for the interaction of the first and second molecules. This third molecule will most commonly be a protein. It may exert its effect by stabilizing the interaction between the first and second molecules or by forming a connection between them when they otherwise would not interact.

In a preferred embodiment, this third molecule may also interfere with the interaction of the first two. For, instance, if all of the molecules are proteins, the third molecule may contain a polypeptide that is identical or similar to the bait or prey polypeptides. Thus, the third molecule will interfere with the ability of the bait and prey to interact. This variation of the two-hybrid assay is commonly known as a inhibition or competition two-hybrid assay. It is especially amenable to the method of the present invention because such assays do not currently provide precise results. Thus, inhibition two-hybrid assays would benefit greatly from the present invention because relative amounts of the bait and prey polypeptides greatly influence the ability of the third molecule to inhibit the bait-prey interaction and thus, the sensitivity of the reporter system. The techniques for fine-tuning and varying the amounts of the hybrid proteins of this method might also be applied to regulate the relative or absolute amount of a third inhibition polypeptide in an inhibition two-hybrid assay.

The interaction between the first and second interacting molecules may take place and be detected anywhere within the cell. For instance, it may occur in the nucleus, in the cytoplasm, at or in the membrane, or in an organelle. The system would be expected to work similarly in prokaryotes and eukaryotes, including bacteria, yeast, plant, arthropod, and mammalian cells.

In one preferred embodiment of the present invention, the method is applied to a genetic molecular interaction detection system. Regulation of the amounts of hybrid proteins is accomplished by using compositions comprising alternate promoters for different intrinsic levels of expression of a downstream hybrid protein or molecule. These promoters may be derived from natural or synthetic, yeast or non-yeast sources. Regulation may be accomplished by several methods, including, but not limited to: (a) changing the promoter upstream of a hybrid protein, for instance a hybrid in which the second interacting (prey) polypeptide is derived from a library, to give different levels of expression, as further exemplified below, using a GAL1/10 promoter, CYC1 promoter, or ADH1 promoter, which exhibit different levels of expression (Guarente and Ptashne, 1981; Guarente et al., 1982; Ammerer, 1983; Guarente, 1983; Cantwell et al., 1986); or (b) modifying the promoter itself, as further specified and exemplified below, using a GAL1/10 or CYC1 promoter (or other promoters) with the upstream activating sequences, $UAS_G$ or $UAS_G$, respectively, or other activating sequences, any of which may be positioned at various distances from the transcriptional start sites (West et al., 1984).

In another preferred embodiment of the present invention, regulation of hybrid protein amounts is accomplished by using a single promoter, for example, GAL1/10, CYC1, ADH1 or other natural or synthetic yeast or non-yeast promoters in combination with different upstream enhancer sequences from yeast or non-yeast sources.

In another preferred embodiment, the method of the present invention discloses surprising and unexpected results applicable to all known genetic systems for detecting and analyzing protein interactions with other proteins and with any other classes of molecules. It is clearly and categorically distinguished from the prior art, based on its sensitivity being continuously adjustable; that is, the sensitivity may be adjusted on a plurally stepped dose-responsive basis. This includes, in one preferred embodiment, pharmacologically modifying the transcription or expression of the fusion protein or molecule and detecting the various reporter gene expression levels in a single screen.

This embodiment of the present invention gives major technical advantages including, but not limited to: (a) detecting and analyzing interactions of various strengths, without any prior knowledge of even the range of such interaction strengths; (b) avoidance of biologically non-relevant interactions; (c) the detection of potentially very important but currently systemically undetected, weak interactions; and (d) the potential for actually quantifying the in vivo strength of intermolecular binding, as characteristically defined by dissociation constant (Kd) (Estojak et al., 1995). The practical implications of these and related advantages, include but are not limited to: (a) substantial acceleration of detecting and analyzing protein-molecular interactions; (b) elimination of a large subset of biologically irrelevant but previously detected interactions; (c) detection of biologically important new interactions; (d) the potential for true in vivo estimations and correlations of Kd; (e) substantial enhancement of large-scale commercial screening; and (f) substantially improved effectiveness and efficiency of identifying and elucidating cellular pathways, potential drug targets, potentially complementary drugs, and a variety of other scientifically and commercially important molecular interactions.

In one preferred embodiment of the invention, an extracellular ligand binds and modulates the activity of a specific transmembrane receptor to effect a dose-responsive change in expression or activity of one or more interacting molecules. Examples of such extracellular ligands include but are not limited to growth factors, cytokines, hormones, synthetic agents and biopharmaceuticals and their cellular receptors (Mercurio and Manning, 1999; Baldwin, 1996; Mohal and Sternberg, 1999).

In another preferred embodiment, an intracellular ligand interacts either cytoplasmically or within the nucleus to modulate the expression or activity of the interacting molecules. Examples of such intracellular ligands include but are not limited to small molecular pharmaceutical agents and modulators, including but not limited to antimicrobial agents, anti-tumor agents, nucleic acid-binding agents, cytoskeletal active agents, chelating agents, inducers, co-repressors, and agents affecting intracellular trafficking, localization and protection or degradation (Schena et al., 1991; Rossi and Blau, 1998).

In another preferred embodiment, a membrane-active agent interacts to modulate the level of cellular activation or response potential. Examples of such an agent include but are not limited to ionophores, amphoteric and hydrophobic lipid-active agents and detergents, various anesthetics and solvents, transmembrane and intramembrane signaling agents, and farnesylating agents (Berridge et al., 1999).

In a more preferred embodiment, the amounts of the hybrid proteins containing the bait and/or prey or other proteins and molecules are continuously varied or limited using exogenously activated promoters, exogenous activating agents, and other molecules including, but not limited to: (i) steroid responsive elements (SRE's), including but not limited to those sensitive to natural or synthetic estrogens (e.g., estradiol, estrone and others), androgens, progesterones, glucocorticoids (e.g., dexamethasone, cortisone, hydrocortisone and cortisol, among others), minearlocorticoids, ecdysones, metabolically inactive corticoids, other steroids (e.g., ones complementary to orphan receptors), and retinoids; and/or (ii) agonist and antagonist agents in combination with (i); (iii) any other molecules, receptors and response elements, in any or all combinations effective to provide continuously variable amounts of (iii.a.) a hybrid protein containing the bait polypeptide, (iii.b.) a hybrid protein containing the prey polypeptide, which may have been derived from a library, and/or (iii.c.) generally any molecular expression involved in genetic molecular interaction systems, such as to enable the relevant detection and analysis of the preceding biologically relevant interactions (Schena et al., 1998; Picard et al., 1990; Kralli et al., 1995; Mangelsdorf and Evans, 1995; Kliewer, 1999; Martinez et al., 1999).

Another more preferred embodiment, which forms the basis for the Examples below, comprises a novel Interaction Hybrid System (IHS) which is steroid-hormone-dependent, continuously adjustable, and contains a traditional triple reporter in a *Saccharomyces cerevisiae* two-hybrid system. This relates to and novelly extends the principles and basic design of a yeast two-hybrid system as first presented and patented by Stan Fields (U.S. Pat. No. 5,283,173), which is incorporated by reference herein.

*Saccharomyces cerevisiae* strain yHYB001 was constructed containing auxotrophies for the selectable markers leu2, ade2, trp1, ura3, and arg4. The strain is deltaGAL4 and deltaGAL80, so as to enable the use of the GAL4 DNA-binding domain (GAL4bd) and the GAL4 transcriptional activation domain (GAL4ad) as fusions for two-hybrid interaction detection, exactly as used in the original Fields two-hybrid system. The strain also contains integrated humans estrogen receptor and integrated rat glucocorticoid receptor genes, expressed constitutively. The strain is lem1, which enables the use of decreased concentrations of dexamethasone in yeast, presumably by eliminating a mem brane pump (Kralli et al., 1995). The strain contains three integrated reporters for the detection of two-hybrid interactions. The first is a $UAS_G$-LacZ construct for colorimetric and quantitative assays and screening. The second and third are $UAS_G$-ADE2 and $UAS_G$-LEU2, respectively; these each enable qualitative selection for yeast that contain interacting hybrid proteins or other molecules based on rescue of nutrient auxotrophies.

In this embodiment, in the first hybrid protein, the bait may be fused to the carboxyl-terminal end of the GAL4bd, a DNA binding domain (FIG. 3). This first hybrid protein may be transcribed in a continuous range of amounts over up to five orders of magnitude, and under the influence of an estrogen response element (ERE) within a minimal promoter. This results in variable expression of the bait first hybrid protein over a continuous range of amounts in response to changing levels of estrogen or estrogen antagonists in the yeast growth medium. This promoter-first hybrid protein construct is provided on a two-micron plasmid either under ARG4 or URA3 selection.

Figure 1:
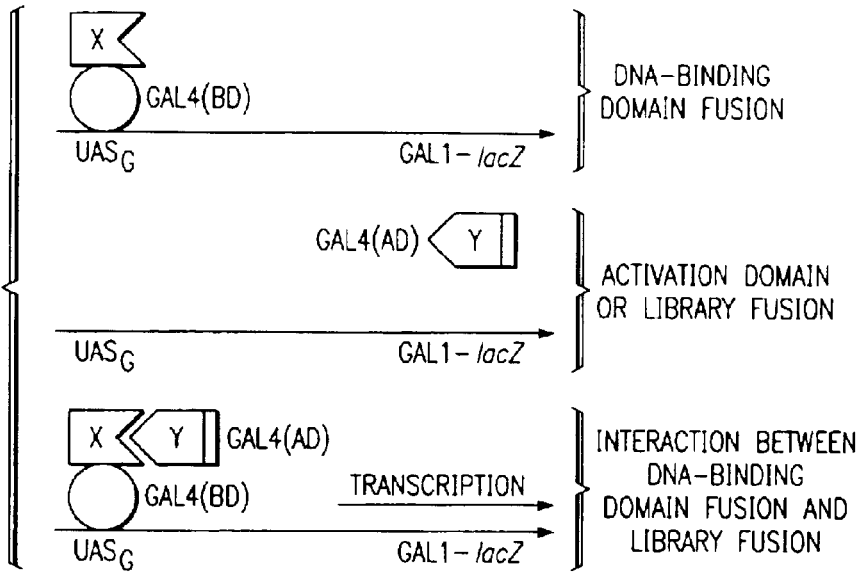
FIG. 1 shows the Original Two-hybrid system relies on the reconstitution of a functional transcription factor to report the interaction of two proteins, depicted as X and Y. The Fields two-hybrid system uses the DNA-binding domain and activation domain from the Gal4p transcription factor (figure adapted from Fields and Song, 1989).
Figure 2:
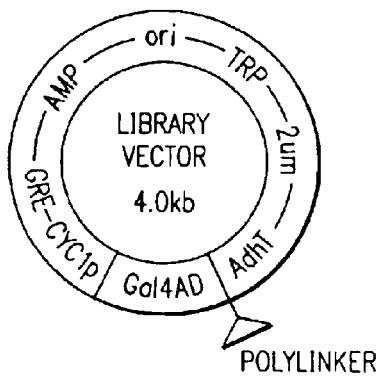
FIG. 2 shows the Novel Library vector described herein is a shuttle vector containing ampicillin and the colE1 origin of replication for selection in *E.coli* as well as TRP1 and the 2 micron origin of replication for selection in yeast. Unknown cDNAs are fused to the Gal4p activation domain, and continuously variable expression is obtained by the induction of GRE upstream activating element(s) attached to CYC1 promoter. AMP=Ampicillin, *E.coli* selectable marker; ori=colE1 bacterial origin of replication; TRP= TRP1 gene, yeast selectable marker; 2 um=origin of replication for yeast; GRE=Glucocortocoid Response Element.

The second hybrid protein may be formed by fusion of the prey polypeptide, which may be derived from a library, to the carboxyl-terminal end of the GAL4ad, a transcriptional activation domain (FIG. 2). This second hybrid protein may be transcribed in a continuous range of amounts over up to five orders of magnitude and under the influence of preferably one to six, and in the present example, three, glucocorticoid response elements (GREs) within a minimal promoter, for example, including but not limited to that from CYC1. This results in variable expression of the second hybrid protein over a continuous range of amounts in response to changing levels of glucocorticoids or their antagonists, including but not limited to dexamethasone, in the yeast growth medium. This promoter-second hybrid protein construct is provided on a two-micron plasmid under TRP1 selection. Both hybrid protein plasmids are also shuttle vectors containing either ampicillin or kanamycin resistance and a colE1 origin of replication, which provide for manipulation in *E. coli* bacteria.

Wide ranges of estrogen and dexamethasone concentrations in the yeast medium result in wide ranges of variable and relative expression of the hybrid proteins. Estrogen is used over a concentration range of at least about $10^{-12}$ to $10^{-8}$ M while dexamethasone is used over a concentration range of at least about $10^{-7}$ to $10^{-4}$ M. Estradiol has some effect on yeast growth above concentrations of $10^{-6}$.

Although only preferred embodiments of the invention are specifically described above, it will be appreciated that modifications and variations of the invention are possible without departing from the spirit and intended scope of the invention.

The following non-limiting examples are provided to more clearly illustrate the aspects of the invention and are not limited to limit the scope of the invention.

EXAMPLES

Example 1

Interaction Hybrid System Adjusted to Give Variable Quantitative Reporter Output without Modifying the Reporter System As noted above, the Brent lab has shown that a given set of two-hybrid protein interactors yield a uniform quantitative reporter output directly proportional to their strength of interaction (Estojak et al., 1995). Utilizing the novel adjustable yeast interaction hybrid system (IHS), introduced and described as a more preferred embodiment in the paragraphs above, three sets of proteins pairs previously demonstrated to interact in a two-hybrid system are demonstrated to give variable levels of reporter output when expressed at different relative concentrations. The level of expression of the first hybrid protein containing the bait is proportional to the concentration of estradiol, and the level of the second hybrid protein containing the prey derived from a library is proportional to dexamethasone concentration (Kralli et al., 1995; Gaido et al., 1997 (FIGS. 4 and 5)).

TABLE 1

Quantitation of known interactors in a traditional Two-Hybrid Screen (2HS) and the novel Interaction Hybrid System (1HS) at various levels of sensitivity

| BAIT HYBRID | LIBRARY HYBRID | TRADITIONAL 2HS | LOW SENSITIVITY 1HS | MEDIUM SENSITIVITY 1HS | HIGH SENSITIVITY 1HS |
|---|---|---|---|---|---|
| SNF1 | SNF4 | 300 | 50 | 250 | 2000 |
| Pelle | Tube | 250 | 20 | 150 | 1400 |
| Pelle | Dorsal | 1300 | 100 | 1400 | 2500 |

*All quantitations of interactions are in Miller units.

Table 1 shows a traditional two-hybrid system and the novel Interaction Hybrid System were done using proteins previously described in Edwards et al. (1997). Methods for analysis of the two-hybrid screen are described in Edwards et al. (1997). Low sensitivity assays in the IHS used $10^{-10}$ M Estradiol and $10^{-7}$ M Dexamethasone. Medium sensitivity assays used $10^{-10}$ M Estradiol and $10^{-5}$ M Dexamethasone. High sensitivity assays used $10^{-12}$ M Estradiol and $10^{-4}$ Dexamethasone.

Table 1 demonstrates that different relative levels of expression of a bait and of a library (prey) hybrid protein in the context of the novel IHS system gives variable levels of reporter activity. Since clearly the Kd of the interaction is not changing, and the sensitivity of the reporter output has not been altered, the quantitative level of expression from the lacZ reporter must be altered by the change in relative concentrations of the hybrid proteins themselves (Table 1).

FIG. 6 is an illustration of the principle of varying reporter output in a genetic interaction system given a constant reporter set. Yeast colonies containing identically hybrid proteins in identical strains were observed to express reporter protein at different levels when exposed to various steroid combinations. Yeast cells containing SNF1 and SNF4 or pelle and tube constructs, fused to the bait and prey vector (respectively, see Table 1), were plated in the corresponding minimal media in the presence of different concentrations of estradiol and or dexamethasone. An integrated copy of $UAS_G$-LacZ was used as a reporter for the interaction. UAS$_G$-LacZ expression was detected by the development of blue color in yeast colonies. Cells grown in plates containing $10^{-12}$M estradiol and $10^{-4}$M dexamethasone showed the highest expression of UAS$_G$-LacZ. At concentrations of $10^{-10}$M estradiol and $10^{-5}$M dexamethasone the level of LacZ expression diminished, being at its lowest when the cells were grown at $10^{-9}$M estradiol and $10^{-7}$M dexamethasone. The different levels of LacZ expression observed corresponded with the sensitivity of the assay, thus at high sensitivity the intensity of the blue color was at its maximum. As the sensitivity of the assay decreased the blue color became less intense. At the weakness level of sensitivity, a light blue color was observed. No blue color developed in yeast colonies containing the prey hybrid alone in the presence $10^{-9}$M estradiol. Similarly, no blue color was observed in yeast colonies containing the bait hybrid alone in the presence of $10^{-4}$M dexamethasone or in yeast colonies with neither prey hybrid nor bait hybrid when grown at in levels of steroids sufficient to produce the highest sensitivity level when both hybrid gene constructs were present.

Example 2

Interaction Hybrid System Adjusted to Low Sensitivity for Promiscuous Bait

When low sensitivity is desired, as in the screening of the mammalian baits IRAK kinase, its Drosophila homolog Pelle kinase, or its plant kinase homologues, high expression of the bait hybrid protein is achieved using $10^{-9}$ M estradiol (for example, as in Table 2, below). Low relative expression of the library prey hybrid proteins is achieved only at $10^{-7}$M dexamethasone (for example, as in Table 2, below). The excess of bait hybrid protein decreases the background expression of weak and irrelevant interactions common to these kinases (refer to FIG. 6). This enables the successful selection, screening and discovery of their respective interactions with activators and scaffolds from a random cDNA library. By muting the background signal, many irrelevant interactions are reduced or eliminated which otherwise would interfere with timely and cost-effective analysis of these screening results.

TABLE 2

Low-sensitivity Screen with Pelle as bait (promiscuous bait)

| Bait | Estradiol | Dexamethasone | Total Positives | False Positives |
|---|---|---|---|---|
| Pelle | $10^{-9}$M | $10^{-7}$M | 5–25 | 0–50%* |
| Pelle | $10^{-10}$M | $10^{-6}$M | 10–50 | 50–90% |
| Pelle | $10^{-11}$M | $10^{-5}$M | 100–500 | 90–95%** |
| Pelle | $10^{-12}$M | $10^{-4}$M | 10,000 | >99% |

*Results are those obtained uniquely in the present example and invention involving promiscuous bait and employing the improved continuously adjustable systemcalibrated to low sensitivity in order to decrease false positives.
**Results are those comparable to ones characteristically obtained using a standard nonadjustable two-hybrid system with no difference in expression between bait and library/prey hybrid proteins.

Table 2 shows utilizing the novel adjustable yeast interaction hybrid system introduced and described as a more preferred embodiment in the paragraphs above, a standard interaction assay on yeast medium is modified to contain various concentrations of steroid substances as shown in Table 2. The readout is total positives comprising the number of colonies surviving selection for interaction. The false positives are colonies containing proteins not interacting with the bait Pelle as determined by separate in vivo or in vitro confirmation assays, including genetic analysis and immunoprecipitation. By comparing the first and third lines of Table 2, it is evident that a maximum of only 13 false positives are obtained in the adjusted low sensitivity screen (see line 1), whereas there are at least 90 false positives observed under screening conditions where there is no difference in expression between bait and library prey hybrid proteins (see line 3). There is no observed decrease in sensitivity to true positives (data not shown). Note: There is no difference between lem 1—1 and wild-type yeast with regard to the response of the estrogen class of steroids (Kralli et al., 1995).

Example 3

Interaction Hybrid System Adjusted to High Sensitivity for Poor Quality Bait

If high sensitivity is desired, as in the screening of the mammalian baits Interleukin-1 receptor, or its Drosophila homolog Toll, or its plant or mammalian homologues, minimal expression of the bait hybrid protein is achieved using $10^{-9}$ M estradiol. High relative expression of the library/prey hybrid protein is achieved using $10^{-5}$ M dexamethasone. The excess of library/prey hybrid protein apparently drives the weak interaction equilibrium toward forming heterodimers; more of the limiting bait hybrid proteins are occupied at a given time by interaction with the abundant library/prey hybrid proteins (FIG. 6). The system thereby detects the weak (high Kd) interaction of these receptors with their cystoskeletal adapter and cytoplasmic proteins.

TABLE 3

High sensitivity Screen with toll Receptor intracellular domain as bait

| Bait | Estradiol | Dexamethasone | Total Positives | False Positives |
|---|---|---|---|---|
| Toll | $10^{-9}$M | $10^{-7}$M | 0 | n/a |
| Toll | $10^{-10}$M | $10^{-6}$M | 0 | n/a |
| Toll | $10^{-11}$M | $10^{-5}$M | 0–5 | 0–50%* |
| Toll | $10^{-12}$M | $10^{-4}$M | 10–30 | 0–50%** |

*Results are those comparable to ones characteristically obtained using a standard nonadjustable two-hybrid system with no difference in expression between bait and library prey hybrid proteins.
**Results are those obtained uniquely in the present example and invention involving poor quality bait and employing the improved, continuously adjustable system calibrated to high sensitivity in order to increase total positives.
n/a: denotes "not applicable" due to no colonies surviving selection.

Table 3 shows using the same modified interaction hybrid system as described above under Example 2, a standard interaction assay on yeast medium is modified to contain various concentrations of steroid substances. The readout is again total positives, comprising the number of colonies surviving selection for interaction. The false positives are colonies containing prey hybrid proteins not likely to interact with the bait Toll based on DNA sequence analysis. By comparing the third and fourth lines of Table 3, it is evident that very few positives result from screens equivalent to the nonadjustable two-hybrid assays characteristic of the prior art (see line 3), whereas, there is a significant increase in positives obtained from the uniquely adjustable high sensitivity screen of the present example (line 4). There is no observed increase in non-specific interactions for this example.

Summarizing Examples 2 and 3, modulation, including continuous and dose-responsive modulation of the expression of bait and library prey hybrid proteins, enables the present, novel interaction hybrid system to detect both weak and strong interactions without the necessity of changing the reporters within the system itself. Strong interactions are not confounded by background levels, and weak interactions are not missed entirely, as characteristically occurs when using standard, nonadjustable interaction hybrid systems.

Example 4

Advantages of Applying the Approach of Example 1 to Expedite the Discovery of Novel Interactors with the Promiscuous Bait, Human Irak 1 Kinase Example 4 demonstrates the markedly improved effectiveness and efficiency of detecting known, functionally relevant and novel interactions with promiscuous bait, including but not limited to human Irak 1 kinase bait. Two parallel sets of screens using Irak 1 as bait, are initiated with either the Roger Brent LexA nonadjustable yeast interaction trap (Gyuris et al. 1993) and with the present adjustable interaction hybrid system. Using lymphocyte cDNA libraries constructed for each system, 10 possible interactions are placed under selection. Positives are yeast colonies surviving selection and therefore containing putative proteins that would interact with Irak 1. Results of the Brent system are ca. 5000 total positives, only 960 of which can be accommodated for further analysis based on the practical limitations of time and cost. By comparison, using the present adjustable system and simultaneously screening at 5 levels of sensitivity, 207 yeast colonies are selected as putative positives at low sensitivity, all of which can be accommodated for further analysis.

Upon analysis of the 960 colonies chosen for workup from the Brent system, 48 represent multiple hits for two separate unique proteins known to interact with Irak1. All other putative positives are random and unrelated proteins designated as false positives. By comparison, upon analysis of all of the 207 colonies passing selection from the present adjustable system, 102 represent the same two unique known proteins, and importantly, two additional positives represent a single unknown protein presumed to be rare in the cDNA library.

Screening and initial analysis using equivalent personnel and materials requires 4 months using the Brent system, but only 4.5 weeks using the present adjustable system. Additionally, based on materials cost alone, the present system affords a ca. five-fold reduction in analytical costs. A parallel five-fold reduction of personnel costs are also achieved based on the reduction in technologist's time required for analytical steps.

Of greatest benefit, is the elimination of random weak interactions, enabling detection of the rare and potentially valuable unknown protein that may be involved in signal transduction of inflammatory signal downstream of the Interleukin 1 receptor.

Example 5

Advantages of Applying the Approach of Example 2 to Expedite the Discovery of Novel Interactors Using a Poor Quality Bait Example 5 elucidates the markedly improved effectiveness of detecting novel interactions with the poor quality bait, human Fc gamma receptor 1 intracellular domain (Fc gamma R1). Two parallel sets of screens using Fc gamma R1 as bait, are initiated with the Roger Brent LexA nonadjustable yeast interaction trap (Gyuris et al, 1993) in comparison with the present adjustable interaction hybrid system. Using lymphocyte cDNA libraries constructed for each system, $10^8$ possible interactions are placed under selection for the standard Brent interaction system and $10^7$ interactions are placed under selection for the present adjustable system. Positives are yeast colonies surviving selection and therefore containing putative proteins that would interact with Fc gamma R1. Results of the Brent system are zero positives, allowing no possibility of further analysis. By comparison, using the present adjustable system and simultaneously screening at 5 levels of sensitivity, 15 yeast colonies are selected as putative positives at highest sensitivity only, all of which importantly are amenable to further analysis. All 15 positives represent copies of a single putative protein interactor, which are candidates for further biochemical and genetic analysis as important modulators of B lymphocyte activation.

Example 6

Commercial and Scientific Relevance

The present adjustable system provides a markedly improved means to obtain cloned DNA sequences together with their corresponding protein structural and functional information for new and known proteins of known and novel functions that can serve as candidate drugs and drug targets. Iterative use of this system enables the improved and accelerated elucidation of entire signaling pathways linking the cell membrane to the nucleus for use in all scientifically and commercially relevant DNA-based organisms. The increased effectiveness and efficiency of screening for protein-protein and other relevant interactions exhibited by the present adjustable interaction hybrid system is potentially widely applicable to enable a markedly increased volume of screens per unit time and cost, as well as mass screening entailing a markedly reduced analytical load. This results in many fewer biologically irrelevant interactors, but retains and increases valuable and biologically important interactors. In turn, this benefits scientific and commercial developments in the fields of medicine, pharmaceutical and biopharmaceutical discovery, agribusiness and bioinformatics, among others. Application of this improved novel technology can potentially markedly enhance the bioinformation of cellular signaling pathways, knowledge of which is becoming essential to the rational development of drugs, antibiotics, biopharmaceuticals, diagnostic, medical interventions and agricultural products, as well a the enhanced elucidation of gene-based disease mechanisms. Hence, this technology potentially provides extended benefits to diverse activities, which utilize leading-edge interaction hybrid systems both academically and commercially. These activities include the elucidation of genomic functional pathways, the rapid correlation of such information with gene sequencing and induced genomic (e.g., RNA expression) assays, and acceleration of the commercial discovery and development of numerous practical genomic products and future applicants.

Example 7

Application to Other Molecular Genetic Detection Systems

The general principle of a reporter having a threshold of detection given a constant level of expression, transcription, or presence for the interactors in question implies the obvious extension of the improvements described herein to all in vivo molecular genetic detection systems. This system would be expected to function identically whether the interactors are proteins, RNA, DNA, carbohydrates, small molecules, drugs, or other potential biological interactors. Extension is also obvious whether the detection of an interaction occurs in the nucleus, in the cytoplasm, within the membranes, or at the membrane of the cell. Finally, the same modifications can be applied to prokaryotic as well as other eukaryotic organisms, including mammalian cell-based two-hybrid systems.

Citations in the following list of References are incorporated in pertinent part by reference herein for the reasons cited in the text.

References

1. Ammerer, G.; 1983. Expression of genes in yeast using the ACDI promoter. Methods in Enzymol. 101, 192–201.

2. Aronheim, A.; Zandi, E.; Hennenmann,, H.; Elledge, S. J.; and Karin, M.; 1993. Isolation of an AP-1 Repressor by a Novel Method for Detecting Protein-Protein Interactions. Mol. Cell. Biol. 17, 3094–3102.

3. Bai, C.; and Elledge, S. J.; 1997. Gene Identification Using the Yeast Two-Hybrid System. Methods Enzymol. 283, 141–156.

4. Baldwin, A. S.; 1996. The NF-κB and IκB Proteins: New Discoveries and Insights. Annu. Rev. Immunol. 14, 649–681.

5. Bartel, P.; Chien, C.; Sternglanz, R.; and Fields, S.; 1993. Elimination of False Positives That Arise in Using the Two-Hybrid System. Biotechniques 14, 920–924.

6. Berridge, P.; Lipp, P.; and Bootman, M.; 1999. Calcium signalling. Curr. Biology 9, R157–R159.

7. Branchmann, R. K.; and Boeke, J. D.; 1997. Tag games in yeast: the two-hybrid system and beyond. Curr. Opin. Biotechnol. 8, 561–568.

8. Bunker, C. A.; and Kingston, R. E.; 1995. Identification of a cDNA for SSRP1, an HMG-box protein, by interaction with the c-Myc oncoprotein in a novel bacterial expression screen. Nucleic Acids Res. 23, 269–276.

9. Bustos, S. A.; and Scleif, R. F.; 1993. Functional domain of the AraC protein. Proc. Natl. Acad. Sci. 90, 5368–5642.

10. Cantwell, B. A.; Brazil, G.; Murphy, N.; and McConnell, D. J.; 1986. Comparison of expression of the endo-β-1,3-1,4-glucanase gene from Bacillus subtilis in Saccharomyces cerevisiae from the CYC1 and ADH1 promoters. Curr. Genetics 11, 65–70.

11. Edwards, D. N.; Towb, P.; and Wasserman, S. A.; 1997. An activity-based dependent network of interactions links Rel protein Dorsal with its cytoplasmic regulators. Development 124, 3855–3864.

12. Estojak, J.; Brent, R.; and Golemis, E. A.; 1995. Correlation of Two-Hybrid Affinity Data with In Vitro Measurements. Mol. Cell. Biol. 15, 5820–5829.

13. Fearon, E. R.; Finkel, T.; Gillison, M. L.; Kennedy, S. P.; Casella, J. F.; Tomaselli, G. F.; Morrow, J. S.; and Van Dang,, C.; 1992. Karyoplasmic interaction selection strategy: A general strategy to detect protein-protein interactions in mammalian cells. Proc. Natl. Acad. Sci. 89, 7958–7962.

14. Fields, S.; and Song, O.; 1989. A novel genetic system to detect protein-protein interactions. Nature 340, 245–246.

15. Finley, R. L.; and Brent, R.; 1997. Two-hybrid analysis of genetic regulatory networks. In: The Yeast Two-Hybrid System. Ed. Bartel, P. L.; Fields, S.; pp. 197–214, Oxford Univ. Press.

16. Gaido, K. W.; Leonard, L. S.; Lovell, S.; Gould, J. C. babai, D.; Portier, C. J.; and McDonnell, D. P.; 1997. Evaluation of chemicals with endocrine modulating activity in a yeast based steroid hormone receptor gene transcription assay. Toxic and App. Pharm. 143, 205–212.

17. Guarente, L.; 1983. Yeast Promoters and lacZ Fusions Designed to Study Expression of Cloned Genes in Yeast. Methods in Enzymol. 101, 181–191.

18. Guarante, L.; and Ptashne, M.; 1981, Fusion of Escherichia coli lacZ to the cytochrome c gene of Saccharomyces cerevisiae. Proc. Natl. Acad. Sci. 78, 2199–2203.

19. Guarente, L.; Yocum, R. R.; and Gifford, P.; 1982. A GAL10 hybrid yeast promoter identifies the GAL4 regulatory region as an upstream site. Proc. Natl. Acad. Sci. 79, 7410–7414.

20. Gyuris, J.; Golemis, E.; Chertkov, H.; and Brent, R.; 1993. Cdi1, a Human G1 and S Phase Protein Phosphatase That Associates with Cdk2. Cell 75, 791–803.

21. Hays, L. B.; Chen, Y-S.A.; and Hu, J. C.; 2000. Two-hybrid screen for characterization of protein-protein interactions in E. coli Biotechniques, 29, 288–294.

22. James, P.; Halladay, J.; and Craig, E. A.; 1996. Genomic Libraries and a Host Strain Designed for Highly Efficient Two-Hybrid Selection in Yeast. Genetics 144, 1425–1436.

23. Kliewer, S. A.; Lehmann, J. M.; and Willson, T. M.; 1999. Orpha Nuclear Receptors: Shifting Endocrinology into Reverse. Science 284, 757–760.

24. Kralli, A.; Bohen, S. P.; and Yamamoto, K. R.; 1995. LEM1, an ATP-binding-cassette transporter, selectively modulates the biological potency of steroid hormones. Proc. Natl. Acad. Sci. 92, 4701–4705.

25. Li, J. J.; and Herskowitz, I.; 1993. Isolation of ORC6, a Component of the Yeast Origin Recognition Complex by a One-Hybrid System. Science 262, 1870–1874.

26. Mangelsdorf, D. J.; and Evans, R. M.; 1995. The RXR Heterodimers and Orphan Receptors. Cell 83, 841–850.

27. Mangus, D. A.; Amrani, N.; and Jacobson, A.; 1998. Pbp1p, a Factor Interacting with Saccharomyces cerevisiae Poly(A)-Binding Protein, Regulates Polyadenylation. Mol. Cell. Biol. 18, 7383–7396.

28. Martinez, A.; Sparks, C.; Drayton, P.; Thompson, J.; Greenland, A.; and Jepson, I.; 1999. Creation of ecdysone receptor chimeras in plants for controlled regulation of gene expression. Mol. Gen. Genet. 261, 546–552.

29. Mendelsohn, A. R.; and Brent, R.; 1994. Applications of interaction traps two-hybrid systems to biotechnology research. Curr. Opin. Biotechnol. 5, 482–486.

30. Mercurio, F.; and Manning, A. M.; 1999. Multiple signals converging on NF-κB. Curr. Opin. Cell. Biol. 11, 226–232.

31. Moghal, N.; and Sternberg, P. W.; 1999. Multiple positive and negative regulators of signaling by the EGF-receptor. Curr. Opin. Cell. Biol. 11, 190–196.

32. Phizicky, E. M.; and Fields, S.; 1995. Protein-Protein Interactions: Methods for Detection and Analysis. Microbiological Reviews, Vol. 59k, No. 1, pp. 94–123.

33. Picard, D.; Khursheed, B.; Garabedian, M. J.; Fortin, M. G.; Lindquist, S.; and Yamamoto, K. R.; 1990. Reduced levels of hsp90 compromise steroid receptor action in vivo. Nature 348, 166–168.

34. Rossi, F. M. V.; and Blau, H. M.; 1998. Recent advances in inducible gene expression systems. Curr. Opin. Biotechnol. 9, 451–456.

35. Schena, M.; Picard, D.; and Yamamoto, K. R.; 1991. Vectors for Constitutive and Inducible Gene Expression in Yeast. Methods in Enzymol. 94, 389–398.

36. Schena, M.; and Yamamoto, K. R.; 1988. Mammalian Glucocorticoid Receptor Derivatives Enhance Transcription in Yeast. Science 241, 965–967.

37. SenGupta, D. J.; Zhang, B.; Kraemer, B.; Pochart, P.; Fields, S.; and Wickens, M.; 1996. A three-hybrid system to detect RNA-protein interactions in vivo. Proc. Natl. Acad. Sci. 93, 8496–8501.

38. Serebriiskii, I.; Khazak, V.; and Golemis E. A.; 1999, A two-hybrid dual system to discriminate specificity of protein interactions. J. Biol. Chem. 274(24), 17080–17087.

39. Shioda, T.; Andriole, S.; Yahata, T.; and Isselbacher, K. J.; 2000. A green fluorescent protein-reporter mammalian two-hybrid system with extrachromasomal maintenance of a prey plasmid: Application to interacting screening. Proc. Natl. Acad. Sci. 97, 5220–5224.

40. Vasavada, H. A.; Ganguly, S.; Germino, F. J.; Wang, Z. X.; and Weissman, S. M.; 1991. A contingent replication assay for the detection of protein-protein interactions in animal cells. Proc. Natl. Acad. Sci. 88, 10686–10690.

41. West, R. W., Jr.; Yocum, R. R.; and Ptashne, M.; 1984. *Saccharomyces cerevisiae* GAL1–GAL10 Divergent Promoter Region: Location and Function of the Upstream Activating Sequence $UAS_G$. Mol. Cell. Biol. 4, 2467–2478.

42. Yang, M.; Wu, Z.; and Fields, S.; 1995. Protein-peptide interactions analyzed with the yeast two-hybrid system. Nucleic Acid Res. 23, 1152–1156.

43. Young, K. H.; 1998. Yeast Two-Hybrid: So Many Interactions, (in) So Little Time . . . . Biology of Reproduction 58, 302–311.

What is claimed is:

1. A method for detecting an interaction between a first test protein and a second test protein at variable sensitivities via a detectable reporter gene, the method comprising:

providing a host cell wherein the host cell comprises a detectable reporter gene capable of expressing a detectable reporter gene product;

providing to the host cell a first hybrid protein comprising a polypeptide region capable of binding DNA and a bait polypeptide derived from the first test protein and a second hybrid protein comprising a polypeptide region capable of transcriptional activation and a prey polypeptide derived from the second test protein, wherein the host cell is additionally provided with the capacity to regulate the absolute or relative amounts of the first and second hybrid protein;

regulating the amounts of the first and second hybrid proteins in a continuously adjustable manner so the detectable reporter gene is activated; and determining the extent to which the detectable reporter gene has been activated whereby an interaction between the first test protein and the second test protein is detected, wherein the first or second hybrid protein is provided by introducing into the host cell a first or second chimeric gene capable of being expressed in the host cell, wherein the first chimeric gene comprises a first exogenously activatable promoter, a sequence coding for a DNA binding region or polypeptide, and a sequence coding for the bait polypeptide, wherein the first exogenously activatable promoter is activated by a first exogenous activator, and wherein the first exogenous activator includes a natural or synthetic metabolically active or inactive steroid, steroid analog or steroid mimic.

2. A method for detecting an interaction between a first test protein and a second test protein at variable sensitivities via a detectable reporter gene, the method comprising:

providing a host cell wherein the host cell comprises a detectable reporter gene capable of expressing a detectable reporter gene product;

providing to the host cell a first hybrid protein comprising a polypeptide region capable of binding DNA and a bait polypeptide derived from the first test protein and a second hybrid protein comprising a polypeptide region capable of transcriptional activation and a prey polypeptide derived from the second test protein, wherein the host cell is additionally provided with the capacity to regulate the absolute or relative amounts of the first and second hybrid proteins;

regulating the amounts of the first and second hybrid proteins in a continuously adjustable manner so the detectable reporter gene is activated; and determining the extent to which the detectable reporter gene has been activated whereby an interaction between the first test protein and the second test protein is detected, wherein the first or second hybrid protein is provided by introducing into the host cell a first or second chimeric gene capable of being expressed in the host cell, wherein the second chimeric gene comprises a second exogenously activatable promoter, a sequence coding for a transcriptional activation domain or polypeptide, and a sequence coding for the prey polypeptide, wherein the second exogenously activatable promoter is activated by a second exogenous activator, and wherein the second exogenous activator includes a natural or synthetic metabolically active or inactive steroid, steroid analog or steroid mimic.

3. The method of one of claims 1 or 2 wherein at least one of the first or second exogenous activators is chosen from the group consisting of cortisol, hydrocortisone, estrogen, estradiol, estrone, progesterone, androgen, ecdysone, retinoid, steroids which bind to orphan receptors, mineralocorticoid and mineralocorticoid analogues, and combinations thereof.

4. A method for detecting an interaction between a first test protein and a second test protein at variable sensitivities via a detectable reporter gene, the method comprising:

providing a host cell wherein the host cell comprises a detectable reporter gene capable of expressing a detectable reporter gene product;

providing to the host cell a first hybrid protein comprising a polypeptide region capable of binding DNA and a bait polypeptide derived from the first test protein and a second hybrid protein comprising a polypeptide region capable of transcriptional activation and a prey polypeptide derived from the second test protein, wherein the host cell is additionally provided with the capacity to regulate the absolute or relative amounts of the first and second hybrid proteins;

regulating the amounts of the first and second hybrid proteins in a continuously adjustable manner so the detectable reporter gene is activated; and determining the extent to which the detectable reporter gene has been activated whereby an interaction between the first test protein and the second test protein is detected, wherein the host cell is from *Saccharomyces cerevisiae* strain comprising three integrated promoters for the detection of two-hybrid interactions, the first integrated reporter being a construct yielding a quantifiable product, the second and third integrated reporters being constructs yielding proteins sufficient to rescue nutrient auxotrophies, wherein the first hybrid protein is provided by
- introducing into the host cell a plasmid containing an ampicillin or kanamycin resistance gene, a colE11 origin of replication and a DNA sequence encoding a first hybrid protein comprising a bait polypeptide and a Gal4p DNA binding domain, the expression of which is controlled by an integrated estrogen-inducible promoter; and
- inducing expression of the first hybrid protein by incubating the host cell with an exogenous activator capable of activating the promoter; and wherein the second hybrid protein is provided by
- introducing into the host cell a plasmid containing an ampicillin or kanamycin resistance gene, a colE1 origin of replication and a DNA sequence encoding a second hybrid protein comprising a prey polypeptide derived from a library and the carboxy-terminal end of the Gal4p transcriptional activation domain, the expression of which is controlled by a rat gluocoriticoid-inducible promoter; and
- inducing expression of the second hybrid protein by incubating the host cell with an exogenous activator capable of activating the promoter.

* * * * *